(12) United States Patent
Borja et al.

(10) Patent No.: US 6,294,594 B1
(45) Date of Patent: Sep. 25, 2001

(54) DENTURE ADHESIVE COMPOSITIONS

(75) Inventors: Michael J. Borja, Keyport, NJ (US); Alan A. Halecky, Glenmoore, PA (US)

(73) Assignee: Block Drug Company, Inc., Jersey City, NJ (US)

(*) Notice: Subject to any disclaimer, the term of this patent is extended or adjusted under 35 U.S.C. 154(b) by 0 days.

(21) Appl. No.: 09/660,068

(22) Filed: Sep. 12, 2000

(51) Int. Cl.$^7$ ................ A61K 6/00; C08L 1/20
(52) U.S. Cl. ............ 523/120; 424/78.2; 424/78.24; 424/486; 424/487; 523/105; 523/108; 524/35; 524/37; 524/48; 524/55; 524/56; 524/275; 524/277; 524/284; 524/558; 525/185; 525/328.9
(58) Field of Search .................... 525/185, 328.9; 524/35, 37, 45, 48, 55, 56, 275, 277, 284, 558; 424/486, 487, 78.2, 78.24; 523/105, 108, 120

(56) References Cited

U.S. PATENT DOCUMENTS

| | | | |
|---|---|---|---|
| 2,978,812 | 4/1961 | Rosenthal | 32/2 |
| 3,003,988 | 10/1961 | Germann | 260/33.6 |
| 5,001,170 | 3/1991 | Keegan | 523/120 |
| 5,880,172 | 3/1999 | Rajaiah et al. | 523/120 |
| 6,069,188 | 5/2000 | Rajaiah et al. | 523/120 |

FOREIGN PATENT DOCUMENTS 1 444 485    7/1976   (GB).

*Primary Examiner*—Samuel A. Acquah
(74) *Attorney, Agent, or Firm*—Nora Stein-Fernandez; Stephen A. Venetianer; Charles M. Kinzig

(57) ABSTRACT

A denture adhesive base composition consisting essentially of polyvinyl pyrrolidone and ethylene oxide polymer. A denture adhesive composition including this base composition is also provided with other optional adhesive components. Also is provided a method for formulating a novel denture adhesive base composition consisting essentially of polyvinyl pyrrolidone and ethylene oxide polymer.

20 Claims, 3 Drawing Sheets

DENTURE ADHESIVE COMPOSITIONS

BACKGROUND OF THE INVENTION

1. Field of the Invention

The present invention is directed to denture adhesives or stabilizers, and particularly to an improved denture adhesive composition.

2. Description of the Prior Art

Traditionally, dentures within the mouth were secured by using adherent powders prepared from natural gum materials such as karaya, acacia or tragacanth gum. These materials have the property of swelling to many times their original volume upon the addition of water to form a gelatinous or mucilaginous mass. Cream forms of the adherent, prepared from finely ground particles of the gums, were also available and used instead of the powder composition.

Over the years, there have been numerous improvements over the above-described simple denture adhesive formulations. U.S. Pat. No. 2,978,812 discloses a denture fixative composition which includes an ethylene oxide polymer having a molecular weight between 50,000 and 5,000,000 in an amount preferably comprising at least 50% of the active fixative material. GB Patent No. 1,444,485 discloses a fixing agent comprising a solution of 4 to 44 wt. % of a polyvinyl pyrrolidone ("PVP"). U.S. Pat. No. 3,003,988 describes the use of mixed salts of more than 40 wt. % of a water-insoluble water-sensitized polymeric material consisting essentially of lower alkyl vinyl ether maleic anhydride polymers. U.S. Pat. No. 5,001,170 discloses a substantially anhydrous mixture of about 20 40 wt. % methyl vinyl ether maleic acid copolymer, 20–40 wt. % of PVP, and 20–40 wt. % of ethylene oxide polymer.

The use of ethylene oxide polymer, or polyethylene oxide ("PEO"), has declined recently, being supplanted by metal crosslinked polymers which exhibit greater strength. Recent improvements include the use of a lower alkyl vinyl ether maleic acid, anhydride, or salt polymer or mixtures thereof and one or more metallic salts selected from the group consisting of calcium, magnesium, strontium, sodium, potassium, zirconium, and zinc or mixtures thereof. U.S. Pat. No. 5,830,933 discloses a denture adhesive composition with about 15–55 wt. % of a salt of a copolymer of maleic acid or anhydride.

Applicants have found that by simply complexing PEO chains to PVP molecules surprisingly improve the cohesive strength of PEO, yielding denture adhesive formulations comparable to formulations based on salts of polymaleic acid methyl vinyl ether in sensory tests as well as cohesive strength, without the need for metal crosslinked polymer systems.

SUMMARY OF THE INVENTION

A denture adhesive formulation consisting essentially of a denture effective amount of polyethylene oxide ("PEO") and polyvinyl pyrrolidone ("PVP"). In one embodiment of the invention, the composition consists essentially of from about 15 to 75 wt. % PVP and from about 5 to 40 wt. % PEO. In another embodiment, the composition consists essentially of from about 20 to 70 wt. % PVP and 10 to 30 wt. % PEO.

The invention also relates to a method for adhering a denture to the oral mucosa resulting from the use of the new composition of the present invention.

DETAILED DESCRIPTION OF THE INVENTION

Figure 1:
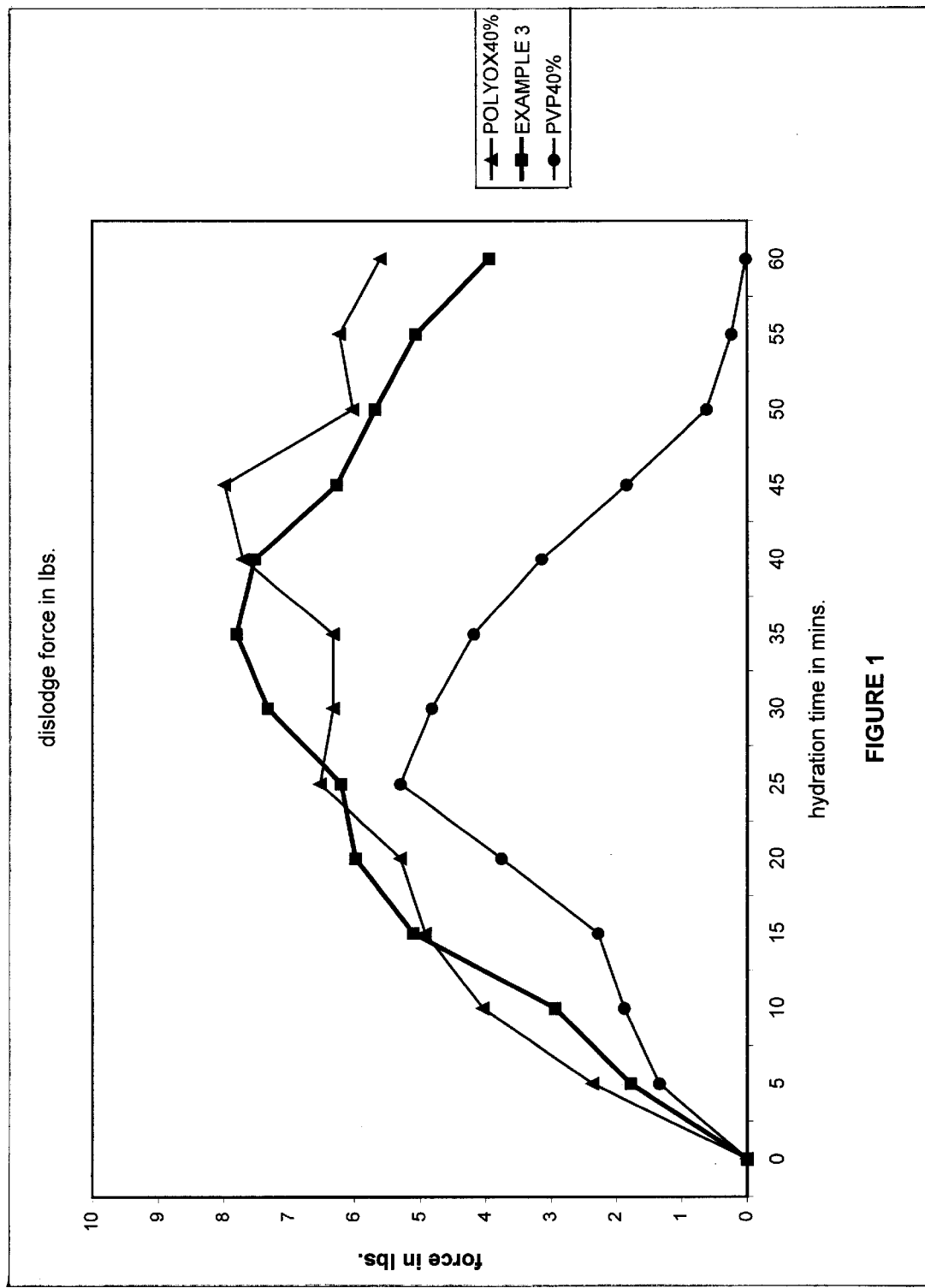
FIGS. 1, 2 and 3 are graphs of adhesive force in lbs. vs. the hydration time in minutes, comparing the adhesive composition of the invention with comparative examples.

Applicants have unexpectedly discovered a novel denture adhesive composition consisting essentially of two ingredients, polyvinyl pyrrolidone and ethylene oxide polymer, without the need for methyl vinyl ether maleic acid, anhydride, or salt polymers nor the processing step for cross-linking these polymer systems with metal ions.

First component PVP Polyvinyl pyrrolidone, also named providone or PVP, is a known binding and suspending agent which is commercially available. The PVP polymer is typically a polymer of N-vinyl-2-pyrrolidone. In one embodiment, the PVP polymer has a weight average molecular weight of 20,000 to 1,500,000. In another embodiment, the PVP has a weight average molecular weight of 25,000 to 1,500,000, for example, of 25, 30 or 90 of K-value. A commercially available PVP is from BASF under the tradename Kollidon, Mv ca. 1,100,000

Second component PEO The second component of the adhesive formulation is poly(ethylene oxide) or PEO. PEOs are water soluble, non-ionic, polyether homopolymers having molecular weights from about 100,000 to about 5,000,000. The homopolymers are white powders which when hydrated develop into a gelatinous mass having adhesive characteristics. The polyether polymers have the chemical structure—$(CH_2CH_2O)_n$—wherein n represents the degree of polymerization of the polymer and may have a value from about 2,000 to about 100,000. PEOs of the type employed in the present invention are more fully described in "Polyox," 1978, published by Union Carbide Corporation, New York, N.Y., as Technical Bulletin F-44029B. PEOs useful in the invention include linear, water soluble polyethylene oxides as well as crosslinked PEOs. PEOs are commercially available from Union Carbide Corporation under the trademark Polyox.

The above two components are used in safe and adhesively effective amount, which herein means an amount sufficient to provide adherence to the oral cavity. In general, the composition consists essentially of from about 15 to 75 wt. % PVP and from about 5 to 40 wt. % polyethylene oxide. In one embodiment, the denture adhesive composition consists essentially of from about 20 to 50 wt. % PVP and 5 to 30 wt. % polyethylene oxide for a cream formulation. In one embodiment of a denture liner formulation, the composition consists essentially of from about 20 to 70 wt. % PVP and 5 to 20 wt. % polyethylene oxide Optional adhesive components In addition to the two ingredients as indicated above to prepare the adhesive base, the composition may optionally contain other components to aid in enhancing the adhesive nature of the base components, including those commonly known and used in the adhesive art.

The composition of the present invention is effective in adhering a denture to the oral mucosa without the need to include any methyl vinyl ether maleic acid, anhydride, or salt of the copolymers within. However, these ingredients and equivalents thereof may be included although it is not necessary to do so.

Suitable optional adhesive components include the traditional water-soluble hydrophilic colloids or polymers having the property of swelling upon exposure to moisture to form a mucilaginous mass. These materials include copolymers of maleic acid or maleic anhydride or salts thereof, natural gums, synthetic polymeric gums, synthetic polymers, mucoadhesive polymers, hydrophilic polymers, saccharide derivatives, cellulose derivatives, and mixtures thereof.

Examples of such materials include karaya gum, guar gum, gelatin, algin, sodium alginate, tragacanth, chitosan, acrylamide polymers, polyacrylic acid derivatives sold under the trademark Carbopol®, polyvinyl alcohol, polyamines, polyquartemary compounds, polybutenes, silicones, cationic polyacrylamide polymers.

In one embodiment, the optional adhesive components are cellulose derivatives in the form of a full or partial salt such as methylcellulose, sodium carboxymethylcellulose, hydroxyethylcellulose, hydroxypropylcellulose, hydroxypropylmethylcellulose, carboxy-methylcellulose. In another embodiment, the optional components are carboxymethylcellulose, karaya gum, sodium alginate, chitosan, polyvinyl alcohol, and mixtures thereof. In general, the other adhesive components may be present at a level of from about 0% to about 70%. In one embodiment, they are from about 5% to about 50%. In another embodiment, they are from about 2% to about 20% by weight of the composition.

Optional ingredients and excipients In addition to the foregoing materials, the denture adhesive composition may be formulated with additional components well-known in the denture adhesive art including waxes, oils, preservatives, flavoring agents, colorants, sweetening agents, viscosity modifiers and so forth.

The waxes useful in the invention comprise both natural and synthetic waxes and include without limitation animal waxes such as beeswax, lanolin and shellac wax, vegetable waxes such as carnauba, candelilla and bayberry wax, mineral wax such as petroleum waxes including paraffin, and microcrystalline.

The oils useful in the invention include without limitation mineral oil, vegetable oil such as corn, soybean, cottonseed, castor, palm and coconut oils and animal oil such as fish oil, and oleic acid.

Flavoring agents well known to the denture adhesive art may be added to the compositions of the present invention. These flavoring agents may be chosen from synthetic flavor oils and/or oils derived from plants, leaves, flowers, fruits and so forth, and combinations thereof. Representative flavor oils include: spearmint oil, cinnamon oil, oil of wintergreen (methylsalicylate) and peppermint oils. Also useful are artificial, natural or synthetic fruit flavors such as citrus oil including lemon, orange, grape, lime and grapefruit, and fruit essences including apple, strawberry, cherry, pineapple and so forth. The flavoring agent may be a liquid, spray dried, encapsulated, adsorbed on a carrier and mixtures thereof. A preferred flavoring agent is peppermint oil. The amount of flavoring agent utilized may vary depending on such factors as flavor type, adhesive formulation and strength desired. In general, amounts of about 0.01% to about 5.0% by weight of the total denture adhesive composition are usable. In one embodiment of the invention, amounts of about 0.05% to 0. 15% are used.

Preservatives which may be used in the denture adhesive formulations of the invention include those known antimicrobial agents conventionally employed in the art, such as benzoic acid and sodium benzoate; the parabens; sorbic acid and sorbates; propionic acid and propionates; acetic acid and acetates; nitrates and nitrites; sulfur dioxide and sulfites; antibiotics; diethyl pyrocarbonate; epoxides; hydrogen peroxide; and phosphates. The parabens include the methyl, ethyl, propyl, and butyl esters of parahydroxybenzoic acid. Methyl paraben and propyl paraben are the preferred preservatives of the invention, utilized in amounts of about 0.03% to about 0.6% by weight of the total denture adhesive composition.

The denture adhesive compositions may also include the use of sweeteners well known in the art. The sweetening agent may be selected from a wide range of materials including water-soluble agents, water-soluble artificial sweeteners, and dipeptide based sweeteners, including mixtures thereof. Representative sweeteners include: a) water-soluble sweetening agents such as monosaccharides, disaccharides and polysaccharides such as xylose, ribose, glucose, mannose, galactose, fructose, dextrose, sucrose, sugar, maltose, partially hydrolyzed starch, or corn syrup solids and sugar alcohols such as sorbitol, xylitol, mannitol, maltitol, hydrogenated starch hydrolysate and mixtures thereof; and b) water-soluble artificial sweeteners such as the soluble saccharin salts, i.e., sodium or calcium saccharin salts, cyclamate salts, acesulfam-K, sucralose and the like, and the free acid form of saccharin; and c) Dipeptide based sweeteners such as L-aspartyl-L-phenylalanine methyl ester and the like. In general, the amount of sweetener may be about 0.001% to about 5% by weight of the final denture adhesive composition.

The colorants useful in the present invention include the pigments such as titanium dioxide, and may also include dyes suitable for food, drug and cosmetic applications. These colorants are known as F.D. & C. dyes. Illustrative examples include indigo dye, known as F.D. & C. Blue No. 2, which is the disodium salt of 5,5'-indigotindi-sulfonic acid; F.D. & C. Green No. 1, comprises a triphenylmethane dye and is the monosodium salt of the 4-[4-Nethyl-p-sulfobenzylamino) diphenylmethylene]-[1-(N-ethyl-N-P-sulfobenzyl)-2,5-cyclohexadienimini]. A preferred colorant is F.D. & C. Red No. 3.

The viscosity modifiers useful herein include quaternary ammonium compounds and similar agents, starches, gums, casein, gelatin and semisynthetic cellulose.

The composition of the present invention may also be used as a denture adhesive and/or bioadhesive and comprise one or more therapeutic actives suitable for mucosal or topical administration. The phrase "suitable for mucosal or topical administration," as used herein, describes agents which are pharmacologically active when absorbed through internal mucosal surfaces of the body such as the oral cavity, or applied to the surfaces of the skin. Therapeutic actives may be present at a level of from about 0% to about 40% by weight of the composition.

Therapeutic actives that are useful in these compositions include antimicrobial agents such as iodine, sulfonamides, bisbiguanides, or phenolics; antibiotics such as tetracycline, neomycin, kanamycin, metronidazole, or clindamycin; anti-inflammatory agents such as aspirin, acetaminophen, naproxen and its salts, ibuprofen, ketorolac, flurbiprofen, indomethacin, eugenol, or hydrocortisone; dentinal desensitizing agents such as potassium nitrate, strontium chloride or sodium fluoride; anesthetic agents such as lidocaine or benzocaine; antifingals; aromatics such as camphor, eucalyptus oil, and aldehyde derivatives such as benzaldehyde; insulin; steroids; and anti-neoplastics. It is recognized that in certain forms of therapy, combinations of these agents in the same delivery system may be useful in order to obtain an optimal effect. Thus, for example, an antimicrobial and an anti-inflammatory agent may be combined in a single delivery system to provide combined effectiveness.

Preparation The denture adhesive compositions may be in the form of a powder, a paste or cream form, or a liner form. The means for preparing such formulations is well known in the denture adhesive art, employing conventional types of mixing equipment for blending, heating, and cooling solids and liquids. In one embodiment, mixing is performed at temperatures suitable to melt the components, i.e., petrolatum, to be blended.

In the powder form, the components are admixed with flavoring agents and colorants, together with other ingredients such as non-toxic anti-caking agents (silica, magnesium stearate, talcum powder or the like). The mixture of ingredients is thoroughly agitated or stirred to yield a generally homogenous intermixing of all components.

In the cream or paste formulation, the components are admixed with petrolatum along with the previously described waxes, oils, preservatives, flavoring agents, colorants, sweetening agents, viscosity modifiers and so forth.

In the liner or layer form, the components are uniformly mixed and then coated onto a non-adhesive self-supporting coating layer by any conventional coating techniques, such as by spraying (if the material is liquid or slurry or dissolved or suspended in a liquid such as water) or by sifting (if the denture adhesive is in powder form). In another embodiment, the components are admixed with the previously described waxes, oils, preservatives, flavoring agents, colorants, sweetening agents, viscosity modifiers and so forth. The liner is then formed by any of a variety of techniques known in the polymer film-forming art, including casting, calendaring, coating, and extrusion. In one embodiment to form liners, the components are first mechanically softened by a ring roller; smoothed on a hydraulic press; and die-cut as desired into denture liner shapes or other desired shapes.

To further illustrate the invention, examples are set forth below. In these, as throughout the specification and claims, all parts and percentages are by weight and all temperature in degree centigrades unless otherwise indicated.

EXAMPLES 1–3

Adhesive Force Evaluation 2 g. samples of each of the following prepared powder compositions were evaluated for adhesion characteristics by adhesive force testing called the "Dislodge Force Method." This test method involves the use of two plates, an upper plate and a lower plate, in a water bath at about 37° C. The upper plate is lined with felt (representing the maxilla) and attached to a Chatillon® gauge and moving ram. The lower plate is made out of polymethyl methacrylate (representing the denture) and attached onto a hinge which is attached to a Chatillon® test stand. As the upper plate applies downward pressure, the lower plate swings downward onto the hinge. This action simulates the biting motion of the mouth. The swinging motion of the lower plate simulates the dislodgement of a denture.

In this test, four stripes of adhesive with about 0.125 grams of adhesive per stripe are applied onto the lower plate. The two plates are then brought together under 10 lbs. compression force for 5 minutes. At the end of the 5 minutes, compression is removed and the upper plate is lowered at a rate of 25 mm per minute. A force (representing the first dislodge force reading) is registered by the Chatillon® gauge. During this cycle, the downward swinging motion of the lower plate represents dislodgment. This compression, decompression, and reading cycle is repeated again for 11 more times, giving a total of 12 cycle readings of 5 minutes each, or a total of 60 minutes hydration time. Recording (dislodge force in lbs.) for the 1st, 2nd, 3rd, . . . , 12th cycle were recorded and then plotted graphically in the Figures.

| Components | Comparative Example 1 | Comparative Example 2 | Present invention Example 3 |
|---|---|---|---|
| Polyvinyl pyrrolidone K90 | — | 40 | 30 |
| Polyox 301 100 mesh | 40 | — | 10 |
| CMC 7H3SXF | 10 | 10 | 10 |
| Petrolatum | 50 | 50 | 50 |

Figure 2:
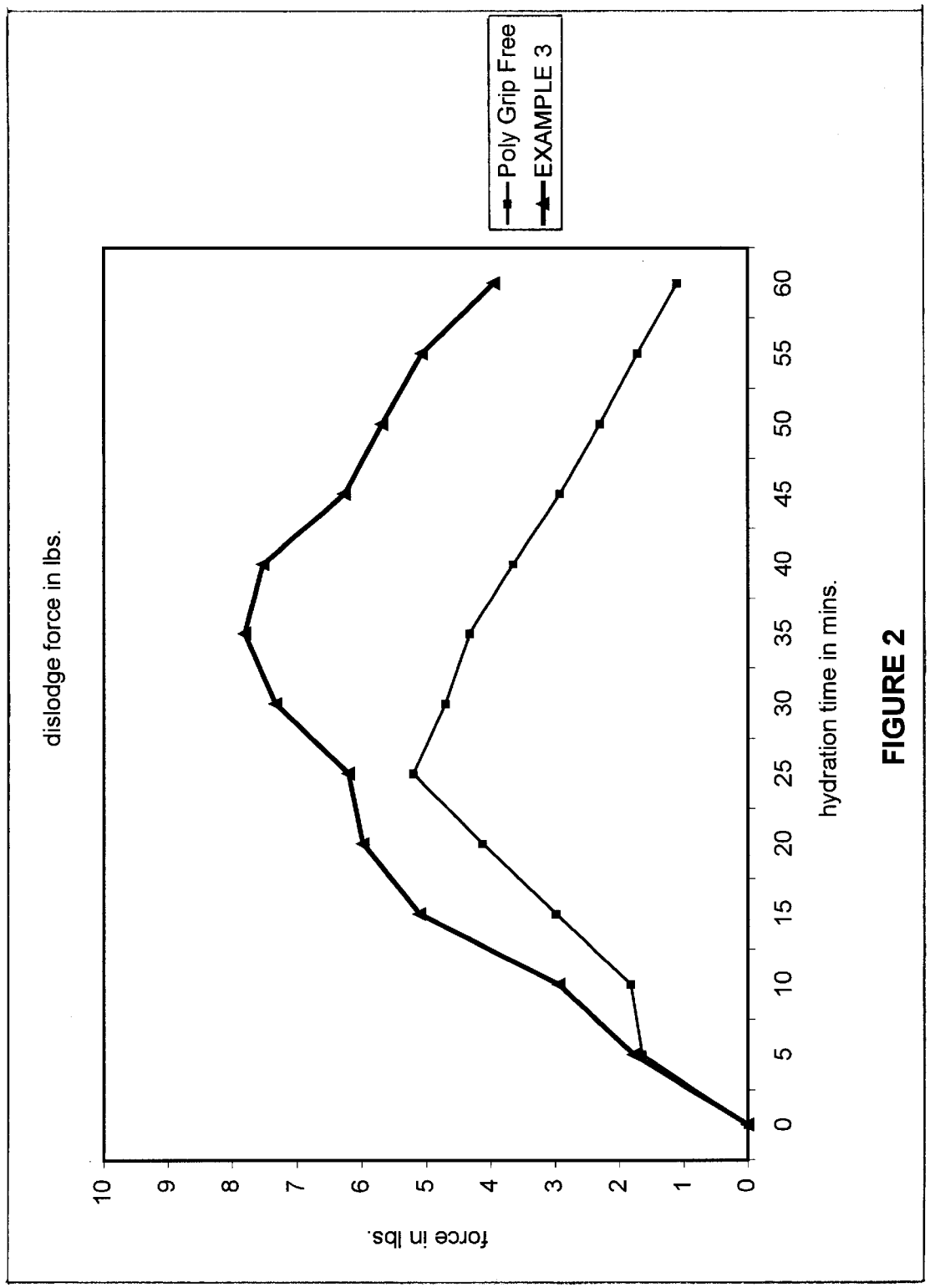
Figure 3:
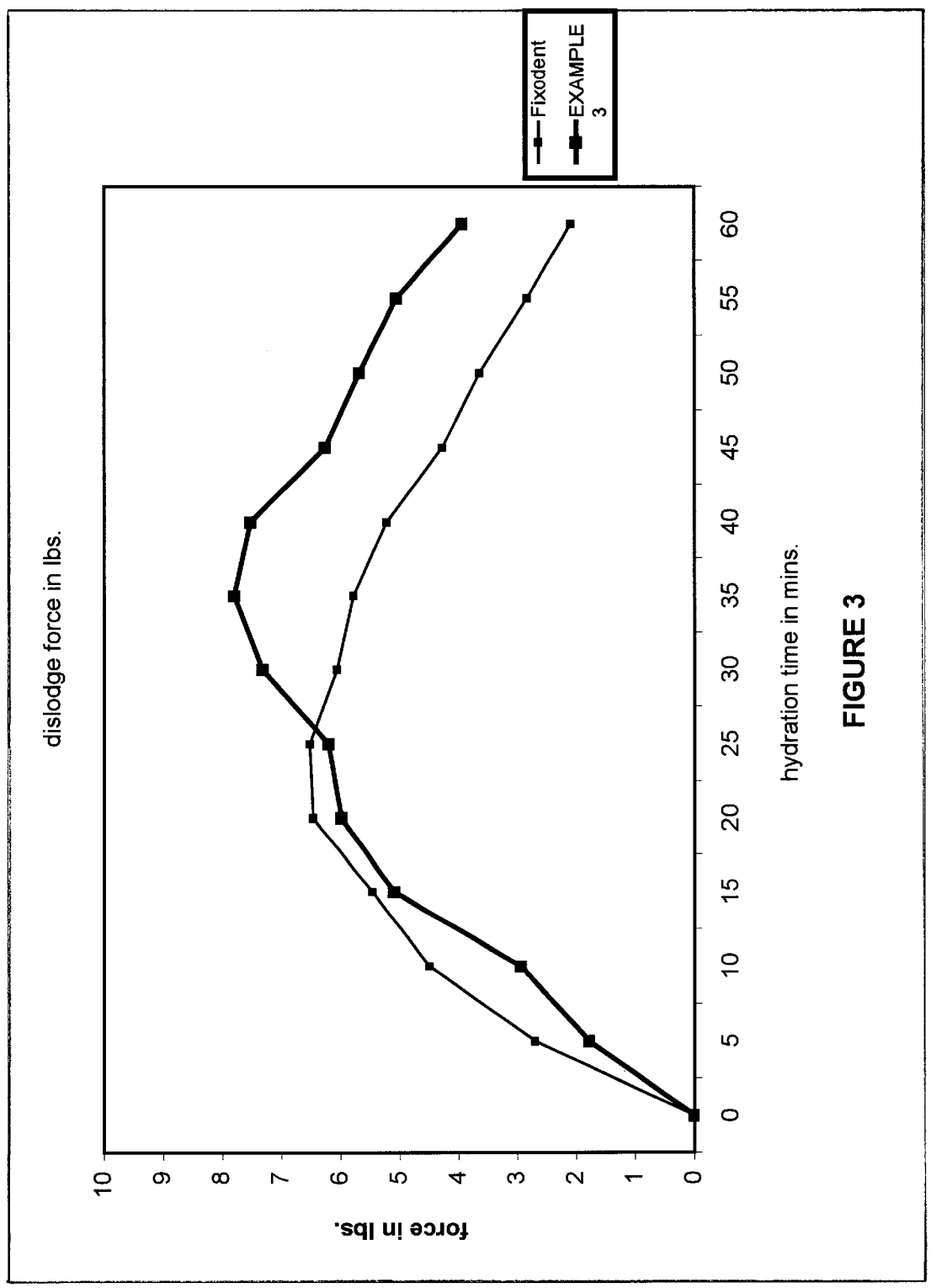

FIG. 1 compares the PVP / Polyox composition of the present invention (Example 3) with Comparative Examples 1 (with Polyox) and 2 (with PVP). FIG. 2 compares the composition of the present invention (Example 3) with a commercially available denture adhesive composition, Polygrip® comprising metal salts of methyl vinyl ether/maleic acid or anhydride copolymers or Gantrez®. FIG. 3 compares the PVP / Polyox composition of the present invention (Example 3) with a commercially available denture adhesive composition, Fixodent®, also known to contain metal salts of methyl vinyl ether/maleic acid or anhydride copolymers or Gantrez®.

EXAMPLE 4

Cream Formulation

In this example, the PVP and Polyox powders are mixed together and added to the melted petrolatum, mineral oil, and Carbopol® in a KitchenAid mixer with stirring. The flavors and dyes are added and intimately mixed in for about 30 minutes. The resultant denture adhesive composition is a viscous material which turns into a smooth soft mass upon wetting and mixing with water or saliva.

| | |
|---|---|
| Polyvinyl pyrrolidone K90 | 30.00 |
| Polyox 301 100 mesh | 10.00 |
| CMC 7H3SXF | 10.00 |
| Mineral Oil | 18.55 |
| Petrolatum | 29.00 |
| Carbopol ® 981NF | 1.00 |
| Silicon dioxide | 1.00 |
| SD peppermint flavor | 0.20 |
| SD spearmint flavor | 0.20 |
| D&C Red #7 | 0.02 |
| D&C Red #30 | 0.03 |
| Total | 100.00 |

EXAMPLE 5

Denture Liner Formulation

For this formulation, polyethylene oxide powder is first admixed with PVP in a kitchen aid mixer and then added to a mixture of Carbopol® and methyl cellulose. The blend is dissolved with an appropriate amount of water and extruded forming a film. A typical denture liner formulation is as follows:

| | |
|---|---|
| Kollidon PVP K90 | 58.00 |
| Polyox 301 100 mesh | 10.00 |
| CMC 7H3SXF | 10.00 |

-continued

| | |
|---|---|
| Carbopol ® 981NF | 1.00 |
| Deionized water | 30.00 |
| Total | 100.00 |

EXAMPLE 6

Sensory Evaluation

The denture cream formulation in example 4 was tested against commercially available denture adhesive cream formulations containing metallic crosslinked methyl vinyl ether maleic acid copolymer. The sensory tests were carried out to evaluate the organoleptic characteristics of the polyethylene oxide / polyvinyl pyrrolidone formulation of the present invention against leading market denture adhesives.

In organoleptic evaluation tests, several expert evaluation panels of twenty-five panelists total were presented with two samples of denture adhesive creams. One was the formulation of the present invention, the other was the commercial formulation. The panelists were asked to fill-out a questionnaire to evaluate the denture creams based on fifteen different criteria, e.g., mouth feel, hold property, time hold property develops, etc. Statistical analyses of the tests indicate that the denture formulation of the present invention was judged to provide denture stabilizing properties comparable to commercial formulations comprising metal salts of methyl vinyl ether/maleic acid or anhydride copolymers or Gantrez®. It was also found that the denture formulation of the present invention did not exhibit any objectionable phase separation or oozing from a dental plate.

Applicants intend to cover, in the appended claims, modifications that are within the scope of the present invention.

What is claimed:

1. A denture adhesive base composition consisting essentially of:
   a) from about 15 to 75 wt. % polyvinyl pyrrolidone and
   b) from about 5 to 40 wt. % ethylene oxide polymer.

2. The denture adhesive base composition of claim 1, wherein said polyvinyl pyrrolidone is about 20 to 70 wt. %, and said ethylene oxide polymer is about 5 to 20 wt. %, based on the total weight of the denture adhesive base composition.

3. The denture adhesive base composition of claim 2, wherein said polyvinyl pyrrolidone is about 40 to 70 wt. %, and said ethylene oxide polymer is about 5 to 20 wt. %, based on the total weight of the denture adhesive base composition.

4. The denture adhesive base composition of claim 2, wherein said polyvinyl pyrrolidone is about 20 to 50 wt. %, and said ethylene oxide polymer is about 5 to 20 wt. %, based on the total weight of the denture adhesive base composition.

5. The denture adhesive base composition of claim 3, wherein said polyvinyl pyrrolidone is present in amounts of from about 25 to 40 wt. %, and said ethylene oxide polymer is present in amounts of from about 5 to 20 wt. %, based on the total weight of the denture adhesive base composition.

6. The denture adhesive composition of claim 1 in the form of a cream formulation.

7. The denture adhesive composition of claim 1 in the form of a denture liner.

8. The denture adhesive composition of claim 1, further including from about 0 to about 70 percent by weight, based on the total weight of the denture adhesive composition, of additional materials selected from the group consisting of: cellulose derivatives, polyacrylic acid derivatives, sodium alginate and mixtures thereof.

9. The denture adhesive composition of claim 8, further including from about 0 to less than 20 percent by weight, based on the total weight of the denture adhesive composition, of a lower alkyl vinyl ether maleic acid, anhydride, or salt polymer or mixtures.

10. The denture adhesive composition of claim 8, wherein the cellulose derivatives comprises carboxymethyl cellulose.

11. The denture adhesive composition of claim 9, further including additional materials selected from the group consisting of waxes, oils, preservatives, flavoring agents, colorants, sweetening agents, viscosity modifiers and mixtures thereof.

12. The denture adhesive base composition of claim 9, further including non-toxic, powdered, excipient materials.

13. A method for preparing a denture adhesive composition comprising:
   a. preparing a substantially anhydrous mixture consisting essentially of from about 15 to 75 wt. % polyvinyl pyrrolidone and from about 5 to 40 wt. % ethylene oxide polymer;
   b. forming a denture adhesive composition including said denture adhesive base composition; and
   c. recovering said denture adhesive composition.

14. The method of claim 13, wherein said denture adhesive composition further includes up to about 70 percent by weight, based on the total weight of the denture adhesive composition, of additional materials selected from the group consisting of: cellulose derivatives, polyacrylic acid derivatives, sodium alginate and mixtures thereof.

15. The method of claim 14, wherein said cellulose derivatives comprise carboxymethyl cellulose.

16. The method of claim 14, wherein said denture adhesive composition further including additional materials selected from the group consisting of waxes, oils, preservatives, flavoring agents, colorants, sweetening agents, viscosity modifiers and mixtures thereof.

17. A process for the preparation of the denture adhesive composition of claim 1, wherein the denture adhesive composition is mechanically softened and pressed smooth and cut into denture shapes.

18. A denture stabilizing composition consisting essentially of a safe and adhesively effective amount of two components: a) polyvinyl pyrrolidone and b) ethylene oxide polymer.

19. The denture adhesive composition of claim 18, further including from about 0 to about 70 % by weight, based on the total weight of the denture adhesive composition, of additional materials selected from the group consisting of: cellulose derivatives, polyacrylic acid derivatives, sodium alginate and mixtures thereof.

20. The denture adhesive composition of claim 19, further including from about 0 to less than 20% by weight, based on the total weight of the denture adhesive composition, of a lower alkyl vinyl ether maleic acid, anhydride, or salt polymer or mixtures.

* * * * *